United States Patent [19]
Mattox

[11] Patent Number: 5,200,188
[45] Date of Patent: Apr. 6, 1993

[54] WATER-DILUTABLE ISOTHIAZOLONE COMPOSITIONS

[75] Inventor: John R. Mattox, Perkasie, Pa.

[73] Assignee: Rohm and Haas Company, Philadelphia, Pa.

[21] Appl. No.: 586,063

[22] Filed: Sep. 21, 1990

[51] Int. Cl.$^5$ ............................................. A01N 25/00
[52] U.S. Cl. .................................... 424/405; 424/406; 424/407; 424/417; 424/418; 424/420
[58] Field of Search ............... 424/405, 406, 407, 417, 424/418, 420

[56] References Cited

U.S. PATENT DOCUMENTS 4,954,338  9/1990  Mattox .................................. 424/78

OTHER PUBLICATIONS

Remingtons Pharmaceutical Sciences, Alfonso R. Bennero, 1985, pp. 314 and 327–329.

Primary Examiner—Thurman K. Page
Assistant Examiner—William E. Benston
Attorney, Agent, or Firm—Michael B. Fein

[57] ABSTRACT

A water-dilutable preservative (antimicrobial) concentrate comprising an isothiazolone, a first solvent capable of solubilizing the isothiazolone and having a specific gravity <0.95, a second solvent capable of solubilizing the isothiazolone and having a specific gravity >0.95, and an emulsifier is disclosed. The isothiazolone emulsive concentrates of the invention may be formulated to produce physically stable emulsions.

19 Claims, 2 Drawing Sheets

WATER-DILUTABLE ISOTHIAZOLONE COMPOSITIONS

BACKGROUND OF THE INVENTION

1. Field of Invention

This invention relates to a water-dilutable preservative concentrate and to an emulsion prepared therefrom for preserving fabric, wood, timber, leather, and various films generated from polymer latices.

2. Description of the Prior Art

Preservatives are often used in conjunction with the manufacture of fabrics, wood products, leather, and other substrates subject to microbial attack. Attack by fungi and bacteria can lead to discoloration and/or degradation of the substrate. Often the preservative is applied by dilution into water and subsequent dipping of the article to which the preservative is applied. In addition, the preservative can be prediluted in water or added directly to a liquid matrix to preserve subsequent films formed upon drying of the matrix, i.e., polymer emulsions or paints.

If the preservative is water insoluble it is often combined with water immiscible solvents and emulsifiers so that on addition to water an emulsion forms in which the preservative is, at least initially, uniformly dispersed in the aqueous medium. It is known to incorporate such preservatives, e.g., isothiazolones with fungicidal properties such as those marketed by Rohm and Haas Company as Kathon biocides, into the treatment mixture.

A problem which has been noted in applications which involve dipping a substrate, such as fabric, wood, leather, and the like, into emulsions of isothiazolone fungicides, is that the isothiazolone may be taken up by the substrate in a non-uniform manner due to poor homogeneity of the emulsion. Related problems occur where emulsions are used to impregnate wood. This is accomplished by introducing the isothiazolone emulsion into a vessel containing the wood to be impregnated, and applying pressure and vacuum according to various defined procedures. The emulsion not taken up by the wood is pumped into a storage tank where is remains, with little or no agitation, until reused to impregnate subsequent batches. Often the stored emulsion must remain unagitated during non-use periods, or overnight, weekends, etc. Emulsions which are prepared and held unagitated, before addition to polymer laticies or paints have the same homogeneity problems. The problem is especially acute in situations where the emulsion is prepared and used over a period of weeks with little or no agitation. Separation of emulsions can lead to overdosing or underdosing the preservative.

One approach to solving the problem of inhomogeneity caused by separation of the oil phase with time is to formulate a microemulsion, such as described in U.S. Pat. No. 4,954,338. The small particle size (<1000 A) of the microemulsion precludes phase separation but typically requires five to ten times the amount of emulsifier needed to form macroemulsions. It has been observed that high emulsifier levels can sometimes be detrimental to retention of isothiazolone on the preserved substrate when the substrate (fabric, wood, leather, and the like) subsequently comes into contact with water during use or storage. High levels of emulsifier can solubilize water insoluble preservative resulting in loss of a portion of the isothiazolone and a lesser degree of preservation than expected from a given concentration of isothiazolone. The degree of solubilization is dependent upon the amount of emulsifier present. It is usually desirable to minimize the amount of emulsifier present as regards the loss of preservation on subsequent exposure to water.

It is known to use a mixture of isothiazolones, emulsifiers, and organic solvents to prepare emulsive concentrates of isothiazolones for dilution into aqueous systems. However, these emulsive concentrates do not possess good "phase stability" (lack of phase separation) upon being diluted; one factor contributing to the tendency of these mixtures to undergo phase separation is the large density differential that exists between the isothiazolone/solvent phase and the aqueous phase.

It is known to use a mixture of agricultural pesticides-/insecticides/herbicides, emulsifier, and organic solvents for dispersal and/or dilution into aqueous solutions for applications to crops, plants, soil, and the like. Commercially used pesticide emulsive concentrates are usually considered satisfactory and adequate if they do not phase separate within one to two hours after dilution, because agitation is usually present during application.

In the case where solvents alone are used to dissolve the isothiazolone preservative, known as the "isothiazolone concentrate", the concentrate is diluted on site into the aqueous treatment solution for dipping of a substrate or impregnation of wood. Solvents used to make up conventional isothiazolone concentrates are typically of the low density (specific gravity <0.9), aromatic hydrocarbon type, e.g., xylene. These solvents possess the necessary solubility characteristics to dissolve significant amounts of water-insoluble isothiazolones such as 4,5-dichloro-2-n-octyl-3-isothiazolone. These particular isothiazolone concentrates also contain a small amount of emulsifier in order to produce a dispersion/emulsion once the concentrate is diluted into the aqueous solution to be used to treat the wood. Due to the large density differential between the solvent concentrate and the aqueous solution in which the concentrate is being diluted, the resultant emulsion of isothiazolone very often is unstable in terms of homogeneity, i.e., phase separation occurs between the bulk aqueous phase (specific gravity of approximately 1.00 for water) and the solvent-isothiazolone phase (specific gravity of approximately 0.95). This tendency to phase separate causes problems in repeated use of the aqueous emulsions to treat substrates with isothiazolone preservatives in that within a short time the uptake of isothiazolone into the substrate becomes non-uniform due to non-homogeneous exposure to the isothiazolone. The dip tank method of treating substrates such as fabric, wood, leather, and the like, requires a significant degree of solution/emulsion homogeneity for an extended period of time in order to treat with a precise amount of preservative. Other situations where emulsions of isothiazolones are prepared, used intermittently, and stored without agitation, such as preemulsification before adding to latex, or impregnation of wood, have similar homogeneity requirements.

SUMMARY OF THE INVENTION

We have now surprisingly found that by incorporation of a certain class of organic solvents into the formulation of the isothiazolone emulsive concentrate, that the tendency of the isothiazolone-containing treatment solution (emulsion) to remain homogeneous (stable to phase separation) is greatly enhanced, increasing the period of stability from a few hours to many weeks, thus allowing a high degree of utilization of the isothiazolone "charged" to the system with a uniform uptake by the substrate being treated. Suitable solvents of the invention include lower-alkyl substituted naphthalene, tetralin and lower-alkyl substituted tetralins, indane, and lower-alkyl substituted indanes. Required characteristics are: low water solubility (<0.1% by weight), being a liquid at ambient temperature, good solvency for the isothiazolone (>20% by weight), and a specific gravity of >0.95.

This invention involves a water-dilutable preservative concentrate (emulsive concentrate) having a composition comprising:

(a) an isothiazolone having a water solubility of less than 1% by weight of the formula:

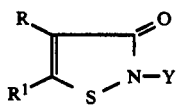

wherein
Y is an unsubstituted alkyl group of 2 to 18 carbon atoms; a substituted alkyl group of 2 to 18 carbon atoms having at least one hydrogen atom replaced by hydroxy, halo, cyano, alkylamino, dialkylamino, phenylamino, halophenylamino, carboxy, carbalkoxy, alkoxy, aryloxy, morpholino, piperidino, pyrrolidonyl, carbamoxy, or isothiazolonyl, wherein the total number of carbon atoms in the substituted alkyl group does not exceed 18; an unsubstituted or halo-substituted alkenyl group of 4 to 18 carbon atoms; unsubstituted or halo-substituted alkynyl group of to 18 carbon atoms; an unsubstituted or alkyl-substituted cycloalkyl group having a four to six carbon atom ring and up to 12 carbon atoms; an unsubstituted or a halo-, lower alkyl-, or lower alkoxy-substituted aralkyl group wherein the total number of carbon atoms in the aralkyl group does not exceed 10; or an unsubstituted or a halo-, nitro-, lower alkyl-, or lower carbalkoxy-, substituted aryl group wherein the total number of carbon atoms in the aryl group does not exceed 10; and R and R¹ are the same or different substituent selected from hydrogen, halogen, or a ($C_1$–$C_4$) alkyl group;

(b) a first organic solvent selected from group consisting of aromatic hydrocarbons having: a kauri-butanol value >70, a boiling range at one atmosphere within the limits 230°–680° F., and a specific gravity of <0.95;

(c) a second organic solvent capable of dissolving at least about 20% by weight of said isothiazolone selected from the group consisting of lower-alkyl substituted naphthalene, tetralin, lower-alkyl substituted tetralins, indane, and lower-alkyl substituted indanes having a specific gravity of >0.95; and (d) an emulsifier selected from the group consisting of octyl phenol ethoxylates, nonyl phenol ethoxylates, primary or secondary alcohol ethoxylates, sorbitan esters, ethoxylated sorbitan esters, ethylene oxide propylene oxide block polymers, ethoxylated fatty acids, ethoxylated castor oil, alkyl sulfates, alkyl aryl sulfonates, sulfonates and sulfates of ethoxylated alkyl phenols, sulfates and sulfonates of oils and fatty acids, phosphates, olefin sulfonates, diphenyl sulfonates, and alkyl benzyl or alkylaryl substituted quaternary ammonium compounds.

Another aspect of the invention comprises preparing the emulsive concentrate such that the final specific gravity of the concentrate matches the specific gravity of the medium to which it is added within the limits ±0.02. For dilution in water, the specific gravity range of the emulsive concentrate would be 0.995–1.005. For dilution in water containing dissolved salts or other solids, the midpoint of the concentrate range would be higher in order to match the specific gravity of the salt solution. For solutions of low density organic materials in water, the midpoint of the range could be less than 1.000.

Another aspect of the invention involves a method for producing a stable emulsion of the diluted isothiazolone emulsive concentrate comprising adding an effective amount (to inhibit microbial growth, such as bacteria, fungi or algae) of the preservative concentrate to a medium in which the concentrate is to be diluted, wherein the specific gravity of the concentrate is within +/−0.02 units of the specific gravity of the medium, preferably within +/−0.01 units, and most preferably within +/−0.005 units.

Another aspect of the invention comprises treating a substrate such as fabric, wood, leather and the like with a preservative composition in an amount effective to inhibit microbial growth comprising a dilution of the isothiazolone emulsive concentrate of the invention into dip tanks or into a predilution tank to be used in wood impregnation or to add to water based materials such as latex, paints, and the like.

DETAILED DESCRIPTION OF THE INVENTION AND THE PREFERRED EMBODIMENTS

Figure 1:
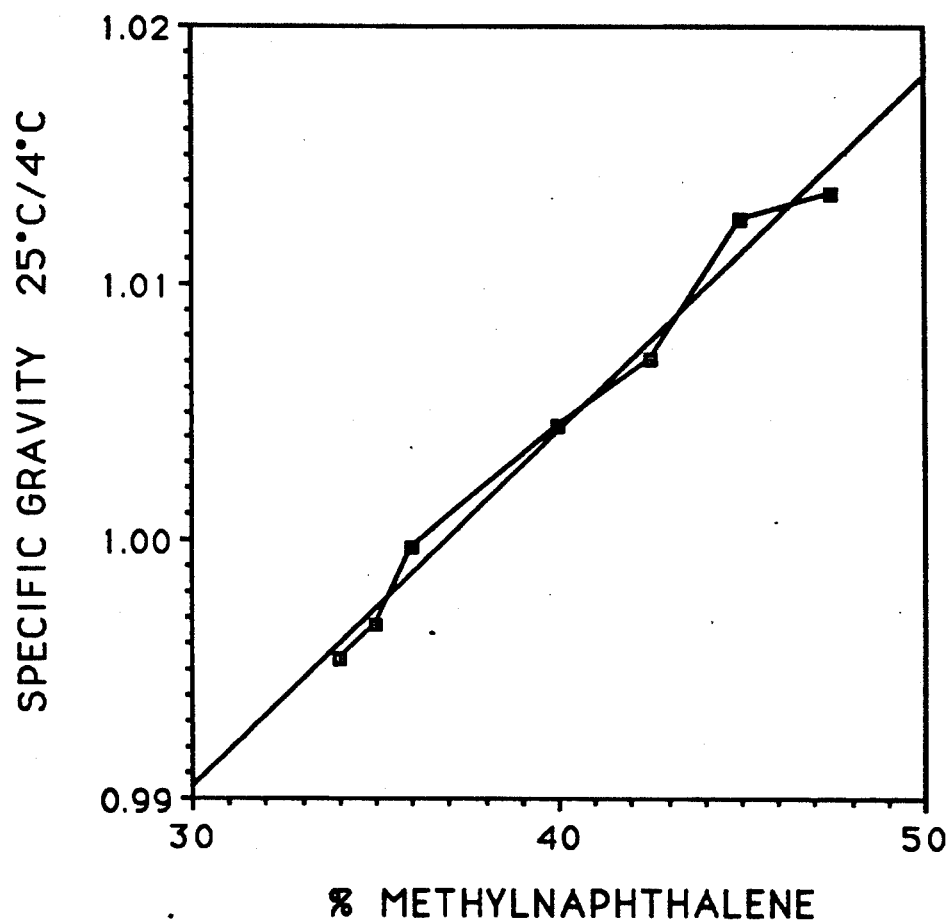
FIG. 1 is a plot of data from Example 1.

Suitable 3-isothiazolones include those having a water solubility of less than 1% by weight of the formula:

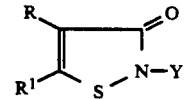

wherein
Y is an unsubstituted alkyl group of 2 to 18 carbon atoms; a substituted alkyl group of 2 to 18 carbon atoms having at least one hydrogen atom replaced by hydroxy, halo, cyano, alkylamino, dialkylamino, phenylamino, halophenylamino, carboxy, carbalkoxy, alkoxy, aryloxy, morpholino, piperidino, pyrrolidonyl, carbamoxy, or isothiazolonyl, wherein the total number of carbon atoms in the substituted alkyl group does not exceed 18; an unsubstituted or halo-substituted alkenyl group of 4 to 18 carbon atoms; unsubstituted or halo-substituted alkynyl group of to 18 carbon atoms, and unsubstituted or alkyl-substituted cycloalkyl group having a four to six carbon atom ring and up to 12 carbon atoms; an unsubstituted or a halo-, lower alkyl-, or lower alkoxy-substituted aralkyl group wherein the total number of carbon atoms in the aralkyl group does not exceed 10; or an unsubstituted or a halo-, nitro-, lower alkyl-, or lower carbalkoxy-, substituted aryl group wherein the total number of carbon atoms in the aryl group does not exceed 10; and R and $R^1$ are the same or different substituent selected from hydrogen, halogen, or a ($C_1$-$C_4$) alkyl group.

One skilled in this art would recognize that the water solubility of the isothiazolones depends on the type of substituent (i.e., R, $R^1$ and Y). For example, the carbon content of the alkyl group will vary depending on the R or $R^1$ or both the R and $R^1$ substituent. As further illustration of what is meant is that, for example, when R=$R^1$=halo, the alkyl group can be as low as two carbon atoms and the water solubility will be less than 1%. When only one of the R or $R^1$ is halo and the other hydrogen, the alkyl group will be at least four carbon atoms. When both R and $R^1$ is hydrogen then the alkyl group must be at least six carbon atoms.

Particularly preferred isothiazolones are 2-n-octyl-3-isothiazolone, 4,5-dichloro-2-cyclohexyl-3-isothiazolone, and 4,5-dichloro-2-n-octyl-3-isothiazolone.

Suitable first organic solvents capable of dissolving the above isothiazolone (>20% by weight and having a specific gravities <0.95) are xylene, Aromatic 100, Aromatic 150, Solvesso 100, Solvesso 150, Shell Sol A, Cyclosol 53, psuedocumene, Panasol AN-2K, Panasol AW-2L, Panasol AN-3N, Cyclosol 27 and Chartersol 1 solvents. Especially preferred are xylene, Solvesso 100 and Solvesso 150 solvent. The Aromatic and Solvesso solvents are supplied by Exxon, the Cyclosol solvents by Shell, the Panasol solvents by Amoco, and the Chartersol solvent by Charter. The kauri-butanol value is a standard measure of aromatic content where values of 80-105 are typical of aromatic compounds (*Hawley's Condensed Chemical Dictionary*, 11th Edition, Von Nostrand Reinhold Co., New York, page 670).

Suitable second organic solvents capable of dissolving the above isothiazolones (>20% by weight) and having specific gravities of >0.95 are lower-alkyl substituted naphthalenes where lower-alkyl refers to ($C_1$-$C_3$)alkyl, tetralin, methyl and dimethyl substituted tetralin, indane, methyl and dimethyl substituted indane. These substituted solvents may contain more than the lower-alkyl substituent so long as the specific gravity of the resultant solvent is >0.95. A preferred solvent is the commercially available mixture of methyl, dimethyl, trimethyl, ethyl, and methyl ethyl substituted naphthalenes known as "methyl naphthalene", hereinafter referred to as methylnaphthalene.

Suitable emulsifiers are those conventionally used in concentrates of isothiazolones: nonionic surfactants such as octyl phenol ethoxylates, nonyl phenol ethoxylates and primary and secondary alcohol ethoxylates; anionic surfactants such as sodium dodecylbenzene sulfonate, calcium dodecyl benzene sulfonate and ethanolamine dodecyl benzene sulfonate. Preferred emulsifiers are selected from commercially available anionic, nonionic blends sold under trade names such as Sponto, Toximul, T-Mulz, and Triton emulsifiers. Sponto emulsifiers are supplied by Witco, Toximul emulsifiers by Stepan, T-Mulz emulsifiers by Thompson-Hayward, and Triton emulsifiers by Rohm and Haas Co. These are especially useful when emulsions must be prepared in a wide range of water hardness.

In the preparation of the emulsive concentrate compositions of this invention, the isothiazolone may be present at 1-35% of the total weight of the concentrate, preferably 5-30%, and most preferably 15-25%. The emulsifiers may be present at 1-12%, preferably 2-10% and most preferably at 3-7%. The amounts of the first (Solvent 1) and second solvent (Solvent 2) are chosen to prepare a concentrate which has a specific gravity to match that of the dilution medium to within ±0.02, preferably ±0.01, and most preferably ±0.005.

The Formulations Table shown below indicates typical ranges for each component of the composition of the invention. The ranges given for Solvent 1 and Solvent 2 represent the various combinations which may be required to most closely match the specific gravity of the dilution medium, given a certain concentration of isothiazolone and emulsifier. The ranges listed in the Formulations Table are capable of matching dilution media specific gravities of up to 1.1, typically 1.05 or less, and most typically 1.02 or less.

| FORMULATIONS TABLE | | | |
|---|---|---|---|
| Isothiazolone | Solvent 1 | Solvent 2 | Emulsifier |
| 1-35% | 0-50% | 5-98% | 1-12% |
| Preferred | | | |
| 5-30% | 3-45% | 15-90% | 2-10% |
| Most Preferred | | | |
| 15-25% | 5-32% | 35-77% | 3-7% |

It is not necessary for the specific gravity of a given composition of the invention to exactly match that of the solution into which it is to be diluted, but that it must be close enough, i.e., within about 0.02 specific gravity units, in order to produce a stable isothiazolone emulsion, i.e., no phase separation after several weeks, after dilution of the isothiazolone emulsive concentrate. The density differentials of prior art formulations for isothiazolone emulsive concentrates using only solvents selected from the group represented by Solvent 1 are typically about 0.05 or greater, thus resulting in poor phase separation resistance, i.e., phase separation after a few hours.

The following examples are illustrative of the invention but are not intended to limit the invention in anyway except as indicated by the claims. Examples 1 and 4 illustrate the wide range of concentrations for each Solvent component at 2 different levels of isothiazolone that would be consistent with matching the specific gravities of dilution media in the range of 0.995 to 1.02. Example 2 presents emulsion stability data on isothiazolone emulsive concentrate compositions of the invention prepared to match the specific gravity of the dilution medium to within +/−0.005 units. Example 3 presents a comparison of the composition of the invention with 2 compositions, one representative of prior art isothiazolone emulsive concentrates in which only solvent selected from the Solvent 1 group is used, and the other representative of an isothiazolone emulsive concentrate using the components of the present invention but not in the ratios required to give a density differential of approximately 0.02 or less specific gravity units relative to the dilution medium being tested.

The following examples refer to concentrations by percent; in all cases this term refers to percent by weight of a given component relative to the total weight of the solution or mixture involved. Isothiazolone A refers to 4,5-dichloro-2-n-octyl-3-isothiazolone. The term active ingredient (designated AI) refers to the isothiazolone component, in this case, Isothiazolone A. The solvents designated Solvesso 100 and 150 are supplied by Exxon UK. The Emulsifier Blends are described in each example and the components are supplied by Witco Co.

EXAMPLE 1

Solvent Composition and Specific Gravity At 25% AI

The following compositions containing 25% active ingredient were prepared and their specific gravities were measured using a pycnometer in a thermostated bath at 25° C. The Emulsifier Blend is composed of 85% Sponto 232T and 15% Sponto 234T emulsifiers.

|  | I | II | III | IV | V | VI | VII |
|---|---|---|---|---|---|---|---|
| Isothiazolone A (94% tech) | 26.5 | 26.5 | 26.5 | 26.5 | 26.5 | 26.5 | 26.5 |
| (As AI) | (25.0) | (25.0) | (25.0) | (25.0) | (25.0) | (25.0) | (25.0) |
| Solvesso 100 | 34.5 | 33.5 | 32.5 | 28.5 | 26.0 | 23.5 | 21.0 |
| Methylnaphthalene | 34.0 | 35.0 | 36.0 | 40.0 | 42.5 | 45.0 | 47.5 |
| Emulsifier Blend | 5.0 | 5.0 | 5.0 | 5.0 | 5.0 | 5.0 | 5.0 |
|  | 100.0 | 100.0 | 100.0 | 100.0 | 100.0 | 100.0 | 100.0 |
| Specific gravity (25/4) | 0.9954 | 0.9967 | 0.9997 | 1.0044 | 1.0071 | 1.0125 | 1.013 |

The data are plotted and the best fit line is shown in FIG. 1.

EXAMPLE 2

Stability of Isothiazolone A Emulsions Toward Phase Separation

In a manner similar to that described in Example 1, Formulation II was prepared except that the Emulsifier Blend used was composed of 80% Sponto 232T and 20% Sponto 234T, hereinafter referred to as Formulation IIA. To each of three 100 ml glass stoppered graduated cylinders was added 99 ml of deionized water (DI), 342 ppm hardness water, and 1000 ppm hardness water, respectively. The two hard water samples were prepared by standard procedures for preparing "standard hard water" (*Specifications for Pesticides*, World Health Organization, p 304 (1973)). To each of the graduated cylinders were added one ml of Formulation IIA (described above). After capping the graduated cylinders they were inverted slowly 30 times and then placed on a level surface with no further agitation. The 3 samples were then observed for phase separation at 2 and 24 hours.

|  | Sample | | |
|---|---|---|---|
| Observation | DI H$_2$O | 342 ppm hardness | 1000 ppm hardness |
| 2-hour | + | + | + |
| 24-hour | + | + | + |
| 8-week | + | + | + |
| 12-week | + | − | − |

"+" = no visible separation
"−" = separation of a cream or oil layer

The emulsion showed excellent stability in a wide range of water hardness for up to 8 weeks. Phase separation occurred in the two hard water samples between 8 and 12 weeks.

The emulsion of formulation IIA in DI water contained in a 100 ml graduated cylinder was sampled after standing 12 weeks unagitated. Samples were taken from the top and bottom 5 mls and analyzed for AI by HPLC. The concentration at the top was 2300 ppm AI and 2600 ppm at the bottom (nominal value expected was 2500 ppm). This demonstrated the visual observation of lack of creaming, i.e., no phase separation.

EXAMPLE 3

Comparative Emulsion Stability Using Single Solvents

In a manner similar to that described in Example 1, formulations IIA, VIII and IX were prepared using the same Emulsifier Blend composition described in Example 2.

|  | VIII | IX |
|---|---|---|
| Isothiazolone A (94% tech) | 26.5 | 26.5 |
| (as AI) | (25.0) | (25.0) |
| Solvesso 100 | 68.5 | — |
| Methylnaphthalene | — | 68.5 |
| Emulsifier Blend | 5.0 | 5.0 |
|  | 100.0 | 100.0 |

These formulations were subjected to the emulsion stability test as described in Example 2 by diluting with DI water (0 ppm hardness).

|  | Sample | | |
|---|---|---|---|
| Observation | IIA | VIII | IX |
| 2-hour | + | + | + |
| 24-hour | + | − | − |

Both VIII and IX underwent phase separation of the oil phase between 2 and 24 hours, whereas formulation IIA showed no separation and would be expected to maintain stability for at least 12 weeks (as shown in Example 2).

The specific gravities of formulations IIA, VIII, and IX are 1.00, 0.94 and 1.04 respectively. Only formulation IIA is capable of a density differential of <0.02 units relative to the dilution water, thus accounting for its excellent phase stability relative to the other formulations.

EXAMPLE 4

Solvent Composition and Specific Gravity

Compositions containing 20% AI Isothiazolone A were prepared containing 3% Emulsifier Blend (same as Example 2) and varying the solvent ratio. Specific gravities were measured as in Example 1.

|  | X | XI | XII | XIII | XIV | XV |
|---|---|---|---|---|---|---|
| Isothiazolone A (95% tech) | 21.0 | 21.0 | 21.0 | 21.0 | 21.0 | 21.0 |
| (as AI) | (20.0) | (20.0) | (20.0) | (20.0) | (20.0) | (20.0) |
| Solvesso 150 | 26.0 | 20.0 | 16.0 | 13.5 | 11.0 | 8.5 |
| Methylnaphthalene | 50.0 | 56.0 | 60.0 | 62.5 | 65.0 | 67.5 |
| Emulsifier Blend | 3.0 | 3.0 | 3.0 | 3.0 | 3.0 | 3.0 |
|  | 100.0 | 100.0 | 100.0 | 100.0 | 100.0 | 100.0 |
| Specific Gravity | 0.998 | 1.008 | 1.011 | 1.012 | 1.017 | 1.018 |

|   | X | XI | XII | XIII | XIV | XV |
|---|---|----|-----|------|-----|-----|
| (25/4) | | | | | | |

Figure 2:
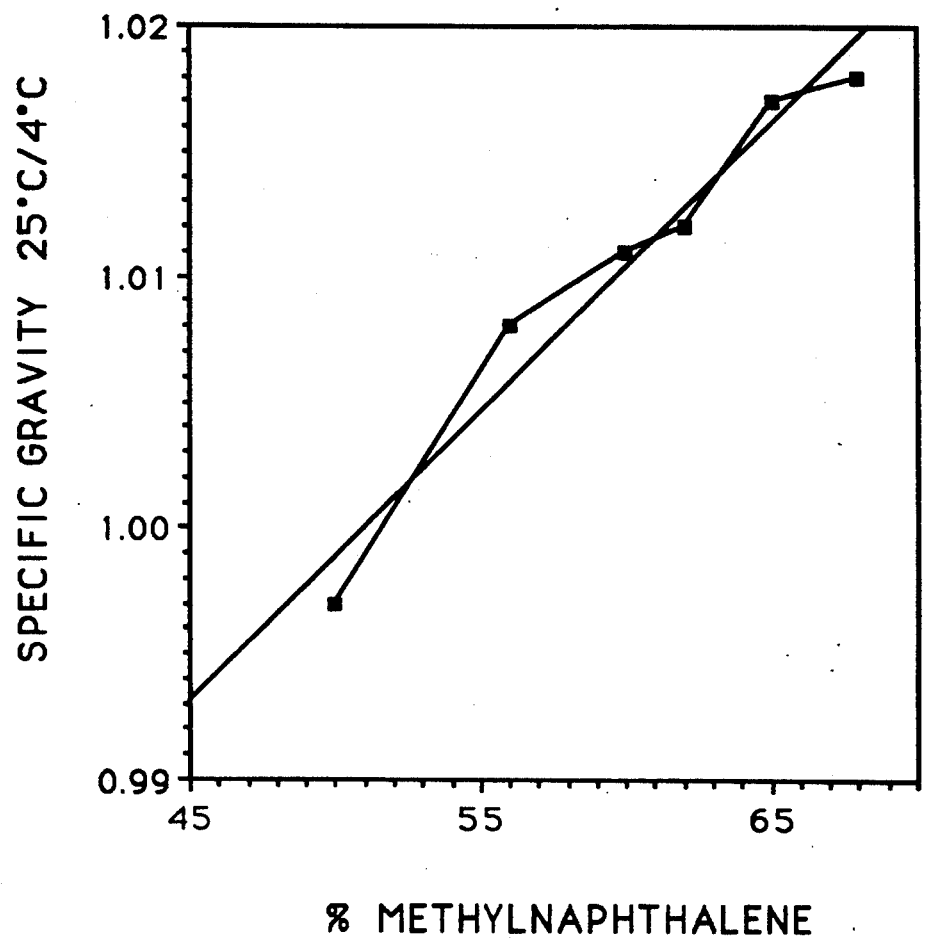
FIG. 2 is a plot of data from Example 4.

The data are plotted and shown in FIG. 2.

I claim:

1. A water-dilutable preservative concentrate composition comprising:
   (a) an isothiazolone having a water solubility of less than 1% by weight of the formula:

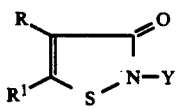

wherein
   Y is an unsubstituted alkyl group of 2 to 18 carbon atoms; a substituted alkyl group of 2 to 18 carbon atoms having at least one hydrogen atom replaced by hydroxy, halo, cyano, alkylamino, dialkylamino, phenylamino, halophenylamino, carboxy, carbalkoxy, alkoxy, aryloxy, morpholino, piperidino, pyrrolidonyl, carbamoxy, or isothiazolonyl, wherein the total number of carbon atoms in the substituted alkyl group does not exceed 18; an unsubstituted or halo-substituted alkenyl group of 4 to 18 carbon atoms; unsubstituted or halo-substituted alkynyl group of to 18 carbon atoms; an unsubstituted or alkyl-substituted cycloalkyl group having a four to six carbon atom ring and up to 12 carbon atoms; an unsubstituted or a halo-, lower alkyl-, or lower alkoxy-substituted aralkyl group wherein the total number of carbon atoms in the aralkyl group does not exceed 10; or an unsubstituted or a halo-, nitro-, lower alkyl-, or lower carbalkoxy-, substituted aryl group wherein the total number of carbon atoms in the aryl group does not exceed 10; and
   R and R$^1$ are the same or different substituent selected from hydrogen, halogen, or a (C$_1$-C$_4$) alkyl group;
   (b) a first organic solvent selected from the group consisting of aromatic hydrocarbons having: a kauri-butanol value >70, a boiling range at one atmosphere within the limits 230°-680° F., and a specific gravity of <0.95;
   (c) a second organic solvent capable of dissolving at least about 20% by weight of said isothiazolone and selected from the group consisting of lower-alkyl substituted naphthalene, tetralin, lower-alkyl substituted tetralins, indane, and lower-alkyl substituted indanes, said second organic solvent having a specific gravity of >0.95; and
   (d) an emulsifier
provided that said composition is in the form of a nonaqueous emulsive concentrate which forms a stable macroemulsion upon dilution with water.

2. The composition of claim 1 wherein the emulsifier is selected from the group consisting of octyl phenol ethoxylates, nonyl phenol ethoxylates, primary or secondary alcohol ethoxylates, sorbitan esters, ethoxylated sorbitan esters, ethylene oxide propylene oxide block polymers, ethoxylated fatty acids, ethoxylated castor oil, alkyl sulfates, alkyl aryl sulfonates, sulfonates and sulfates of ethoxylated alkyl phenols, sulfates and sulfonates of oils and fatty acids, phosphates, olefin sulfonates, diphenyl sulfonates, and alkyl benzyl or alkylaryl substituted quaternary ammonium compounds.

3. The composition according to claim 1 further limited in that said composition has a final specific gravity which matches a specific gravity of a medium to which said composition is added, within the limits +/−0.02.

4. The composition according to claim 1 further limited in that said composition has a final specific gravity which matches a specific gravity of a medium to which said composition is added, within the limits +/−0.01.

5. The composition according to claim 1 further limited in that said composition has a final specific gravity which matches a specific gravity of a medium to which said composition is added, within the limits +/−0.005.

6. The composition according to claim 1 further limited in that said composition has a specific gravity range of about 0.995 to 1.005.

7. The composition according to claim 1 wherein said second organic solvent is selected from the group consisting of lower-alkyl substituted naphthalenes where lower-alkyl refers to (C$_1$-C$_3$)alkyl, tetralin, methyl and dimethyl substituted tetralin, indane, methyl and dimethyl substituted indane.

8. The composition according to claim 7 wherein said second organic solvent is a mixture of methyl, dimethyl, trimethyl, ethyl, and methyl ethyl substituted naphthalene known as methyl naphthalene.

9. The composition according to claim 1 wherein the isothiazolone is selected from the group consisting of 2-n-octyl-3-isothiazolone, 4,5-dichloro-2-cyclohexyl-3-isothiazolone, and 4,5-dichloro-2-n-octyl-3-isothiazolone.

10. A method for producing a stable emulsion comprising adding an effective amount of the preservative concentrate of claim 1 to a medium in which said concentrate is to be diluted, wherein said concentrate has a specific gravity within +/−0.002 units of the specific gravity of said medium.

11. The method of claim 10 wherein the specific gravity of said concentrate is within +/−0.001 units of the specific gravity of said medium.

12. The method of claim 10 wherein the specific gravity of said concentrate is within +/−0.005 units of the specific gravity of said medium.

13. A method for inhibiting the growth of bacteria, fungi, or algae in a locus subject to contamination by bacteria, fungi, or algae, which comprises incorporating onto or into the locus, in an amount which is effective to adversely affect the growth of bacteria, fungi, or algae, the composition of claim 1.

14. The method of claim 13 wherein the locus is an aqueous medium.

15. The method of claim 13 wherein the locus is a solid protective or decorative film.

16. The method of claim 13 wherein the locus is fabric, leather, paper, or wood.

17. The composition according to claim 1 wherein the isothiazolone comprises 1-35% by weight of the composition, the first organic solvent comprises 0-50% by weight of the composition, the second organic solvent comprises 5-98% by weight of the composition and the emulsifier comprises 1-12% by weight of the composition.

18. The composition according to claim 1 wherein the isothiazolone comprises 5-30% by weight of the composition, the first organic solvent comprises 3-45% by weight of the composition, the second organic solvent comprises 15-90% by weight of the composition and the emulsifier comprises 2-10% by weight of the composition.

19. The composition according to claim 1 wherein the isothiazolone comprises 15-25% by weight of the composition, the first organic solvent comprises 5-32% by weight of the composition, the second organic solvent comprises 35-77% by weight of the composition and the emulsifier comprises 3-7% by weight of the composition.

* * * * *